(12) United States Patent
Perego et al.

(10) Patent No.: US 6,380,433 B1
(45) Date of Patent: Apr. 30, 2002

(54) PROCESS FOR THE PRODUCTION OF DIAMINODIPHENYLMETHANE AND ITS HIGHER HOMOLOGUES

(75) Inventors: Carlo Perego, Carnate; Alberto de Angelis, Legnano; Otello Farias, Rome; Aldo Bosetti, Vercelli, all of (IT)

(73) Assignees: Enichem S.p.A., Boldrini; Eni S.p.A., Rome; Enitecnologie S.p.A., Maritano, all of (IT)

( * ) Notice: Subject to any disclaimer, the term of this patent is extended or adjusted under 35 U.S.C. 154(b) by 0 days.

(21) Appl. No.: 09/568,512

(22) Filed: May 11, 2000

(30) Foreign Application Priority Data

May 27, 1999 (IT) .......................................... MI99A1171

(51) Int. Cl.$^7$ ............................................. C07C 211/00
(52) U.S. Cl. ....................................... 564/330; 564/315
(58) Field of Search ................................. 564/315, 330

(56) References Cited

U.S. PATENT DOCUMENTS 5,043,493 A * 8/1991 Neuber et al. .............. 570/202

FOREIGN PATENT DOCUMENTS

| EP | 0 264 744 | 4/1988 |
|---|---|---|
| EP | 0 329 367 | 8/1989 |

* cited by examiner

*Primary Examiner*—Samuel Barts
(74) *Attorney, Agent, or Firm*—Oblon, Spivak, McClelland, Maier & Neustadt, P.C.

(57) ABSTRACT

Process for the production of diaminodiphenylmethane and its higher homologues products, which comprises reacting aniline, or one of its derivatives, and formaldehyde, or a compound capable of producing formaldehyde under the reaction conditions, in the presence of a zeolite in acid form having a spaciousness index ranging from 2.5 to 19.

11 Claims, No Drawings

PROCESS FOR THE PRODUCTION OF DIAMINODIPHENYLMETHANE AND ITS HIGHER HOMOLOGUES

The present invention relates to a process for the production of diaminodiphenylmethane and its higher homologues.

More specifically, the present invention relates to a process for the production of 2,2',2,4' and/or 4,4'-diaminodiphenylmethane and its higher homologous products.

Diaminodiphenylmethane (MDA) is an intermediate for the preparation of diphenylmethane diisocyanate (MDI) which, in turn, is a reagent for the production of polymers based on urethane/urea or epoxy resins. MDA is traditionally prepared from aniline, or from one of its derivatives, by reaction with formaldehyde in the presence of a concentrated solution of a strong acid such as, for example, hydrochloric, sulfuric or phosphoric acid. Literary sources which describe this type of synthesis are: J. Am. Chem. Soc. 57, 888, 1975; Chem. Tech., November 1984, 670; Kirk Othmer, Vol. II, 3$^{rd}$ Edition, 338–348.

The U.S. Pat. No. 5,241,119 describes a process for the preparation of 4,4'-diamino diphenylmethane which comprises the reaction between aniline and formaldehyde in the presence of a solid catalyst selected from zeolites, in particular Y zeolite, ZSM-5 zeolite or zeolites modified with one or more of the following metals: aluminum, boron, iron and titanium. The reaction is carried out in a solvent medium, at a temperature ranging from 50 to 200° C., at a pressure depending on the boiling point of the solvent used.

The Applicant has now found that the preparation of 4,4'-diaminodiphenylmethane, optionally mixed with its 2,2' and 2,4' isomers, together with its higher homologues can be carried out with optimum results using as catalysts medium and large pore zeolites in acid form, partially or totally exchanged.

The object of the present invention therefore relates to a process for the preparation of diamino diphenyl methane, and its higher homologues having general formula (I):

(I)

wherein Φ represents a phenyl group, R represents a hydrogen atom or a $C_1$–$C_8$ (iso)alkyl, $C_4$–$C_{10}$ cycloalkyl or $C_6$–$C_{12}$ aromatic radical, and n is an integer greater than or equal to 1 and is such as to give a functionality ranging from 2 to 4, which comprises the re-arrangement reaction of the intermediate having general formula (II):

Φ—NR—CH$_2$—RN—Φ (II)

in the presence of a zeolite in acid form having a spaciousness index ranging from 2.5 to 19, extremes included.

The spaciousness index is a parameter which provides the real pore width measurement of porous materials, such as zeolites. The spaciousness index is a parameter described in literature such as, for example, in U.S. Pat. No. 4,795,847 or in "Zeolites and Related Microporous Material: State of the Art 1994", Studies in Surface Science and Catalysis, vol. 84, 37, 1994, Elsevier Science B.V.; "Zeolite: Facts, Figures, Future", 1989, 1115, Elsevier Science Publishers, B.V.

According to the present invention, preferred zeolites with a spaciousness index ranging from 2.5 to 19 are those consisting of synthetic crystalline material having the composition (III):

$M_{x/n}{}^{n+}[(AlO_2)^-{}_x(SiO_2)]\cdot(H_2O)_p$ (III)

wherein x is less than 1, p is an integer greater than or equal to 1, generally ranging from 1 to 20, M is a metal of groups IA, IIA, or a lanthanide, n is the valence of M, and wherein M can be partially or totally exchanged with H$^+$ or with the $(NH_4)^+$ ion or with an $(NR'_4)^+$ cation with R' an alkyl radical, for example $C_1$–$C_4$, or an aryl radical.

Examples of zeolite which are included in general formula (III) and have a spaciousness index ranging from 2.5 to 19 are beta zeolite, mordenite, ZSM-12, MCM-22 and ERB-1. The beta zeolite described in U.S. Pat. No. 3,308,069 and having a spaciousness index of 19, is particularly preferred.

The zeolites used as catalysts in the process object of the present invention are preferably in acid form, i.e. in the form in which most of the cationic sites are occupied by hydrogen ions. They can be used as such or modified by the partial isomorphous substitution of aluminum with a metal selected from boron, iron or gallium or mixed with a ligand, for example alumina, and in the form of extruded pellets according to what is described in European patent 847,802.

The re-arrangement reaction takes place at a temperature ranging from 50 to 200° C., preferably from 120 to 20 180° C., in the presence of a solvent, selected from aliphatic or aromatic hydrocarbons or from halogenated aromatic hydrocarbons or aniline. Examples of particularly suitable solvents are aniline and chlorinated aromatic hydrocarbons such as m-dichlorobenzene and chlorobenzene.

The intermediate having general formula (II) is a product which is known in literature, in particular when R is equal to hydrogen (aminal). This intermediate can be obtained by the condensation of aniline, or a derivative of aniline wherein R is different from hydrogen, with formaldehyde, or a compound capable of producing formaldehyde under the reaction conditions. In particular, either formaldehyde in aqueous solution or formaldehyde in oligomeric form (trioxane), pre-dissolved in a solvent, can be used, with molar ratios aniline/formaldehyde ranging from 2 to 10, preferably from 3 to 5. At the end of the synthesis, the intermediate having formula (II) is separated with known techniques such as physical separation, distillation, etc. The product thus obtained can also be used with a water content less than or equal to 3% by weight, preferably less than or equal to 1.5%.

According to an alternative embodiment of the process for the preparation of diamino diphenyl methane having general formula (I), object of the present invention, the rearrangement reaction can be carried out by charging the zeolitic catalyst into a reaction mixture comprising aniline, or one of its derivatives, and formaldehyde, or a compound capable of producing formaldehyde under the reaction conditions. In this alternative case, it is preferable to operate with an excess of aniline, or its derivative, so that it contemporaneously acts as reagent and solvent. It has been observed, in fact, that by using an excess of reagent (aniline) instead of the traditional solvent, it is possible to vary the composition of the end-product, as can be noted from the enclosed examples.

The re-arrangement reaction according to the present invention can be carried out batchwise, in continuous or semi-continuous at atmospheric pressure or at a value which is such as to maintain the reactive system in liquid state.

Some illustrative but non-limiting examples are provided for a better understanding of the present invention and for its embodiment.

EXAMPLE 1—SYNTHESIS OF BETA ZEOLITE 58.8 g of tetraethylammonium hydroxide at 40% by weight in aqueous solution and 1.9 g of sodium aluminate (56% of $Al_2O_3$) are added to 58.4 g of demineralized water. The mixture is heated to about 80° C. and is left under stirring until complete dissolution.

The limpid solution thus obtained is added to 37.5 g of LUDOX HS colloidal silica at 40% by weight of $SiO_2$. A homogeneous suspension is obtained, having a pH equal to 14, which is discharged into a steel autoclave and left to crystallize under hydrothermal conditions at 150° C. for 10 days, under static conditions and autogenous pressure.

The crystallized product is separated by filtration, re-dispersed in demineralized water and re-filtered. A wet zeolite panel is obtained, containing the organic templating agent tetraethylammonium and sodium.

EXAMPLE 2—SYNTHESIS OF BETA ZEOLITE

The wet zeolite panel, prepared as described above, is dried in an oven for 1 hour at 150° C. and calcined in muffle for 5 hours at 550° C. in a stream of air.

The calcined solid is dispersed in an aqueous solution of ammonium acetate (150 g of water and 8 g of ammonium acetate) for the ion exchange. This suspension is heated under stirring for about an hour to 80° C.

The suspension is subsequently filtered and the solid obtained is re-dispersed in demineralized water (150 ml) for washing. The suspension is then filtered and the ion exchange and previous washing are repeated in sequence. The solid is then washed again and dried in an oven for 1 hour at 150° C. thus obtaining the zeolite in ammonia form. This zeolite is calcined in muffle for 5 hours at 550° C. in a stream of air obtaining beta zeolite (spaciousness index=19) in acid form.

From elemental chemical analysis, the sodium residue of this zeolite proves to be 106 ppm whereas the aluminum content is equal to 3.14% ([Al]/[Na]=252).

The product is characterized by means of X-ray diffraction from powders.

EXAMPLE 3—SYNTHESIS OF BETA ZEOLITE

The wet panel obtained in example 1 is re-dispersed in an aqueous solution of ammonium acetate (200 g of water and 16 g of ammonium acetate) for the ion exchange. This suspension is heated under stirring for about an hour to 80° C.

The suspension is subsequently filtered and the solid obtained is re-dispersed in demineralized water (150 cc) for washing. The suspension is then re-filtered and a wet zeolite panel in ammonia/alkylammonia form is again obtained.

From elemental chemical analysis, the sodium residue in this latter sample proves to be equal to 112 ppm. The aluminum content is equal to 3.38% ([Al]/[Na]=257).

The product is characterized by means of X-ray diffraction from powders.

EXAMPLE 4—EXTRUSION OF BETA ZEOLITE

A catalyst is prepared, based on beta zeolite, prepared according to example 3 and consequently not subjected to calcination, and on alumina in the form of bohemite. The catalyst was extruded according to the procedure described in example 4 of the European patent 847,802.

EXAMPLE 5—SYNTHESIS OF ERB-1 ZEOLITE

An alkaline solution consisting of sodium hydroxide is charged into a three-necked 1000 cm³ flask equipped with reflux cooling and rod stirrer. The solution is brought to the temperature value (70–80° C.) by means of a heating jacket, and the aluminum source consisting of sodium aluminate is then added, under stirring, obtaining a limpid solution. The organic templating agent consisting of hexamethyleneimine is added to the reaction mixture and the silica source consisting of Areosil 200 is then slowly added.

| Molar ratios | $SiO_2/Al_2O_3$ | $N/SiO_2$ | $Na^+/SiO_2$ | $OH^-/SiO_2$ | $H_2O/SiO_2$ |
|---|---|---|---|---|---|
| | 30 | 0.35 | 0.18 | 0.18 | 45 |

At the end of the addition, the reaction mixture is maintained under magnetic stirring for about four hours at the above temperature, is then cooled to room temperature and is left in static aging for 24 hours. A homogeneous slurry is obtained, which is charged into a stainless steel autoclave, placed in a weighing oven and kept under weighing stirring conditions for 10 days at a temperature of 150° C.

At the end of the reaction a suspension is discharged, from which a solid is recovered by filtration, which, after repeated washings with demineralized water, is dried in an oven at 120° C. The dried solid is characterized by X-ray diffraction from powders (XRD). The solid is then calcined at 550° C. for 5 hours in a stream of air.

A material is obtained which has the same diffraction spectrum shown in FIG. 4 and table 3 of European patent 293,032.

This material is then exchanged with ammonium acetate and obtained in acid form.

EXAMPLE 6

The intermediate having general formula (II) wherein R is a hydrogen atom (aminal), is prepared by condensation between aniline and formaldehyde. In particular, an aqueous solution at 37% of formaldehyde is charged, under stirring, into a reaction container containing aniline, so as to have a molar ratio aniline/formaldehyde equal to 4. The temperature is gradually increased to 50° C.

At the end of the addition, the mixture is maintained under stirring for 1 hour. The aqueous phase is then separated from the organic phase consisting of aminal and non-reacted aniline, in a separating funnel. The organic phase is subsequently dried until there is a water content of 1.25%, and conserved for subsequent use.

EXAMPLE 7

4 g of aminal, 10 g of m-dichlorobenzene and 250 mg of beta zeolite prepared according to example 2, are charged into a glass autoclave. The autoclave is closed and is maintained under stirring for 6 hours at 150° C.

At the end, the mass is cooled to room temperature and the reaction solvent is removed by distillation at reduced pressure.

The reaction product is analyzed by means of H.P.L.C. with the analysis method described in the Journal für Praktische Chemie, Band 328, Heft 1, 1986, 142–148.
Conversion: 98.54%;
Selectivity to 4,4'-MDA: 46.91%;
Selectivity to 2,4'-MDA: 13.77%;
trimers: 28.64%;
heavy products: 9.22%.

EXAMPLE 8

4 g of aminal, 10 g of aniline, as solvent, and 500 mg of beta zeolite prepared according to example 2, are charged into a glass autoclave. The autoclave is closed and is maintained under stirring for 6 hours at 150° C.

At the end, the mass is cooled to room temperature and the reaction solvent is removed by distillation at reduced pressure.

The reaction product is analyzed by means of H.P.L.C.
Conversion: 98.3%;
Selectivity to 4,4'-MDA: 58.53%;
Selectivity to 2,4'-MDA: 22.88%;
trimers: 5.98%;
heavy products: 9.22%.

EXAMPLE 9

4 g of aminal, 10 g of m-dichlorobenzene and 1 g of mordenite (spaciousness index=7), are charged into a glass autoclave. The autoclave is closed and is maintained under stirring for 6 hours at 150° C.

At the end, the mass is cooled to room temperature and the reaction solvent is removed by distillation at reduced pressure.

The reaction product is analyzed by means of H.P.L.C.
Conversion: 98.70%;
Selectivity to 4,4'-MDA: 51.85%;
Selectivity to 2,4'-MDA: 9.92%;
trimers: 26.75%;
heavy products: 10.18%.

EXAMPLE 10

4 g of aminal, 10 g of aniline and 1 g of mordenite are charged into a glass autoclave. The autoclave is closed and is maintained under stirring for 6 hours at 150° C.

At the end, the mass is cooled to room temperature and the reaction solvent is removed by distillation at reduced pressure.

The reaction product is analyzed by means of H.P.L.C.
Conversion: 98.27%;
Selectivity to 4,4'-MDA: 71.12%;
Selectivity to 2,4'-MDA: 15.13%;
trimers: 6.93%;
heavy products: 5.09%.

EXAMPLE 11

4 g of aminal, 10 g of m-dichlorobenzene and 1 g of ERB-1 (spaciousness index=8) prepared as described in example 5, are charged into a glass autoclave. The autoclave is closed and is maintained under stirring for 6 hours at 150° C.

At the end, the mass is cooled to room temperature and the reaction solvent is removed by distillation at reduced pressure.

The reaction product is analyzed by means of H.P.L.C.
Conversion: 98.70%;
Selectivity to 4,4'-MDA: 45.61%;
Selectivity to 2,4'-MDA: 20.94%;
trimers: 15.33%;
heavy products: 3.45%.

EXAMPLE 12

4 g of aminal, 10 g of aniline and 1 g of ERB-1 are charged into a glass autoclave. The autoclave is closed and is maintained under stirring for 6 hours at 150° C.

At the end, the mass is cooled to room temperature and the reaction solvent is removed by distillation at reduced pressure.

The reaction product is analyzed by means of H.P.L.C.
Conversion: 99.99%;
Selectivity to 4,4'-MDA: 58.98%;
Selectivity to 2,4'-MDA: 22.24%;
trimers: 15.33%;
heavy products: 3.45%.

EXAMPLE 13

4 g of aminal, 10 g of m-dichlorobenzene and 1 g of ZSM-12 (spaciousness index=3) are charged into a glass autoclave. The autoclave is closed and is maintained under stirring for 6 hours at 150° C.

At the end, the mass is cooled to room temperature and the reaction solvent is removed by distillation at reduced pressure.

The reaction product is analyzed by means of H.P.L.C.
Conversion: 98.50%;
Selectivity to 4,4'-MDA: 41.74%;
Selectivity to 2,4'-MDA: 15.07%;
trimers: 29.40%;
heavy products: traces.

EXAMPLE 14

4 g of aminal, 10 g of aniline and 0.5 g of ZSM-12 are charged into a glass autoclave. The autoclave is closed and is maintained under stirring for 6 hours at 150° C.

At the end, the mass is cooled to room temperature and the reaction solvent is removed by distillation at reduced pressure.

The reaction product is analyzed by means of H.P.L.C.
Conversion: 98.34%;
Selectivity to 4,4'-MDA: 54.50%;
Selectivity to 2,4'-MDA: 30.36%;
trimers: 10.76%;
heavy products: 2.87%.

EXAMPLE 15 (Comparative)

4 g of aminal, 10 g of m-dichlorobenzene and 250 mg of ZSM-5 (spaciousness index=1) are charged into a glass autoclave. The autoclave is closed and is maintained under stirring for 6 hours at 150° C.

At the end, the mass is cooled to room temperature and the reaction solvent is removed by distillation at reduced pressure.

The reaction product is analyzed by means of H.P.L.C.
Conversion: 78.80%;
Selectivity to 4,4'-MDA: 7.98%;
Selectivity to 2,4'-MDA: 1.93%;
trimers: 39.85%;
heavy products: 29.85%.

EXAMPLE 16 (Comparative)

4 g of aminal, 10 g of m-dichlorobenzene and 1 g of YH zeolite (spaciousness index=21), commercial sample 320 HOA of Toyosoda, are charged into a glass autoclave. The autoclave is closed and is maintained under stirring for 6 hours at 150° C.

At the end, the mass is cooled to room temperature and the reaction solvent is removed by distillation at reduced pressure.

The reaction product is analyzed by means of H.P.L.C.
Conversion: 83.48%;
Selectivity to 4,4'-MDA: 28.76%;
Selectivity to 2,4'-MDA: 3.48%;
trimers: 31.40%;
heavy products: 19.86%.

EXAMPLE 17

5 cm³ of beta zeolite, prepared according to the procedure described in example 2, compressed at 20 tons and sieved to 70–100 mesh, are charged into a tubular reactor having a diameter of 12.5 mm and a length of 390 mm. A mixture of aminal at 10% by volume in m-dichlorobenzene are then fed to the reactor at a temperature of 180° C., a pressure of 4 bars and an LHSV (Liquid Hourly Space Velocity) of 3.6 h⁻¹, referring to the active phase.

Samples are removed at the times indicated in Table 1, which, after removal at reduced pressure of the solvent, are analyzed according to the method described above.

TABLE 1

| t.o.s. (h) | Conv. % | 4,4'MDA | 2,4'MDA | trimers | heavy products |
|---|---|---|---|---|---|
| 1 | 95.34 | 24.86 | 20.51 | 23.87 | 25.99 |
| 2 | 96.02 | 29.80 | 19.42 | 32.29 | 14.51 |
| 3 | 95.96 | 35.53 | 16.24 | 28.12 | 16.06 |
| 4 | 95.9 | 37.74 | 15.58 | 26.84 | 15.73 |
| 5 | 95.9 | 31.44 | 12.15 | 25.61 | 26.70 |
| 6 | 95.81 | 32.11 | 11.89 | 30.84 | 20.96 |

After 7 hours of reaction, the feeding rate is varied (LHSV=1⁻¹) and the reaction mixture is fed for a total of 25 hours of t.o.s. (time on stream) without there being any sign of deactivation phenomenon. The results are indicated in Table 2.

TABLE 2

| t.o.s. (h) | Conv. % | 4,4'MDA | 2,4'MDA | trimers | heavy products |
|---|---|---|---|---|---|
| 21 | 95.78 | 31.74 | 12.04 | 29.58 | 22.41 |
| 22 | 96.12 | 34.25 | 12.09 | 26.30 | 25.70 |
| 23 | 95.9 | 33.90 | 12.60 | 28.27 | 21.12 |
| 24 | 95.68 | 32.13 | 12.60 | 28.87 | 22.08 |
| 25 | 95.59 | 30.72 | 12.32 | 29.61 | 22.94 |

EXAMPLE 18

10 cm³ of extruded beta zeolite, prepared according to the procedure described in example 4 with a quantity of ligand (Al₂O₃) equal to 50% by weight, which is sieved to 70–100 mesh, are charged into a tubular reactor having a diameter of 12.5 mm and a length of 390 mm. A mixture of aminal at 10% by volume in m-dichlorobenzene are then fed to the reactor at a temperature of 180° C., a pressure of 4 bars and an LHSV of 3.6 h⁻¹, referring to the active phase.

Samples are removed at the times indicated in Table 3, which, after removal of the solvent at reduced pressure, are analyzed according to the method described above.

TABLE 3

| t.o.s. (h) | Conv. % | 4,4'MDA | 2,4'MDA | trimers | heavy products |
|---|---|---|---|---|---|
| 1 | 95.48 | 30.54 | 25.59 | 25.45 | 13.89 |
| 2 | 95.57 | 24.4 | 21.4 | 32.68 | 14.38 |
| 3 | 95.95 | 27.75 | 19.08 | 38.08 | 11.03 |
| 4 | 96.54 | 30.27 | 10.93 | 35.84 | 19.49 |
| 5 | 96.69 | 30.51 | 9.69 | 32.1 | 24.38 |
| 6 | 96.52 | 29.73 | 10.88 | 33.61 | 22.29 |

After 7 hours of reaction, the feeding rate is varied (LHSV=1 h⁻¹) and the reaction mixture is fed for a total of 74 hours of t.o.s. without there being any sign of deactivation phenomenon. The results are indicated in Table 4.

TABLE 4

| t.o.s. (h) | Conv. % | 4,4'MDA | 2,4'MDA | trimers | heavy products |
|---|---|---|---|---|---|
| 21 | 95.58 | 26.82 | 12.74 | 32.97 | 23.05 |
| 22 | 95.64 | 26.52 | 13.2 | 31.78 | 24.13 |
| 23 | 95.55 | 26.77 | 13.42 | 31.37 | 23.98 |
| 24 | 95.47 | 25.49 | 13.67 | 31.28 | 25.03 |
| 25 | 95.47 | 26.39 | 13.9 | 30.45 | 24.72 |
| 26 | 95.58 | 26.30 | 13.57 | 31.27 | 24.44 |
| 46 | 95.65 | 27.93 | 13.45 | 27.07 | 27.19 |
| 47 | 95.40 | 27.35 | 14.34 | 29.00 | 24.70 |
| 49 | 95.40 | 27.95 | 14.47 | 28.30 | 24.68 |
| 50 | 95.48 | 28.15 | 14.17 | 28.08 | 25.08 |
| 51 | 95.59 | 28.63 | 13.68 | 27.24 | 25.93 |
| 52 | 95.42 | 28.19 | 14.41 | 27.95 | 24.87 |
| 53 | 95.17 | 27.27 | 14.39 | 27.52 | 25.99 |
| 69 | 95.O1 | 25.62 | 14.36 | 27.41 | 27.62 |
| 74 | 95.36 | 29.62 | 14.23 | 25.82 | 25.68 |

EXAMPLE 19

10 cm³ of extruded beta zeolite, prepared according to the procedure described in example 4, with a quantity of ligand (Al₂O₃) equal to 50% by weight, which is sieved to 70–100 mesh, are charged into the tubular reactor of the previous example. A mixture of aminal at 10% by volume in aniline are then fed to the reactor at a temperature of 180° C., a pressure of 4 bars and an LHSV of 3.6 h⁻¹, referring to the active phase.

Samples are removed at the times indicated in Table 5, which, after removal of the solvent at reduced pressure, are analyzed according to the method described above.

TABLE 5

| t.o.s. (h) | Conv. % | 4,4'MDA | 2,4'MDA | trimers | heavy products |
|---|---|---|---|---|---|
| 1 | 99.29 | 55.67 | 30.78 | 11.26 | 1.57 |
| 2 | 99.9 | 57.88 | 30.03 | 7.96 | 4.13 |
| 3 | 99.9 | 53.85 | 26.80 | 14.25 | 5.1 |
| 4 | 99.9 | 59.16 | 29.21 | 8.42 | 3.24 |
| 5 | 99.9 | 58.41 | 28.87 | 10.07 | 2.65 |

After 7 hours of reaction, the feeding rate is varied (LHSV=1 h⁻¹) and the reaction mixture is fed for a total of 145 hours of t.o.s. without there being any sign of deactivation phenomenon. The results are indicated in Table 6.

TABLE 6

| t.o.s. (h) | Conv. % | 4,4'MDA | 2,4'MDA | trimers | heavy products |
|---|---|---|---|---|---|
| 22 | 99.9 | 51.24 | 33.19 | 11.98 | 3.59 |
| 23 | 99.9 | 50.87 | 35.12 | 10.44 | 3.51 |
| 24 | 99.9 | 50.98 | 35.97 | 9.94 | 3.11 |
| 26 | 99.9 | 48.15 | 32.97 | 14.9 | 3.98 |
| 28 | 99.9 | 51.45 | 35.86 | 10.4 | 2.29 |
| 46 | 99.9 | 48.23 | 32.88 | 13.83 | 5.06 |
| 48 | 99.9 | 52.32 | 35.58 | 10.33 | 1.80 |
| 50 | 99.9 | 51.89 | 34.88 | 10.6 | 3.15 |
| 54 | 99.9 | 49.69 | 34.06 | 10.56 | 5.68 |
| 56 | 99.9 | 48.51 | 32.91 | 14.53 | 4.04 |
| 72 | 99.9 | 51.78 | 35.24 | 10.06 | 3.16 |
| 74 | 99.9 | 51.04 | 34.32 | 11.3 | 3.33 |
| 76 | 99.9 | 50.77 | 34.14 | 10.78 | 4.30 |
| 78 | 99.9 | 51.40 | 27.82 | 11.34 | 2.43 |
| 145 | 99.9 | 50.46 | 33.83 | 11.97 | 3.73 |

After 145 hours of reaction, the feeding rate is brought to an LHSV value of 3.6 h⁻¹ and the reaction mixture is fed for a total of 192 hours of t.o.s. without there being any sign of deactivation phenomenon. The results are indicated in Table 7.

TABLE 7

| t.o.s. (h) | Conv. % | 4,4'MDA | 2,4'MDA | trimers | heavy products |
|---|---|---|---|---|---|
| 149 | 99.9 | 47.98 | 28.86 | 17.88 | 5.77 |
| 151 | 99.9 | 54.5 | 27.78 | 15.09 | 2.63 |
| 168 | 99.9 | 53.48 | 26.3 | 16.36 | 3.86 |
| 175 | 99.9 | 54.39 | 27.82 | 14.13 | 3.66 |
| 192 | 99.9 | 56.17 | 28.24 | 13.41 | 2.18 |

After 192 hours, the composition of the reaction mixture is varied by feeding aminal at 20% by volume in aniline. The feeding rate remains unvaried and the reaction mixture is fed for a total of 240 hours of t.o.s. without there being any sign of deactivation phenomenon. The results are indicated in Table 8.

TABLE 8

| t.o.s. (h) | Conv. % | 4,4'MDA | 2,4'MDA | trimers | heavy products |
|---|---|---|---|---|---|
| 197 | 99.9 | 51.09 | 25.19 | 17.86 | 5.86 |
| 216 | 99.9 | 52.2 | 23.04 | 19.51 | 5.23 |
| 222 | 99.9 | 51.S1 | 24.78 | 19.38 | 4.31 |

What is claimed is:

1. A process for the preparation of diamino diphenyl methane and its higher homologues having general formula (I):

(I)

wherein Φ represents a phenyl group, R represents a hydrogen atom or a $C_1$–$C_8$ (iso)alkyl, $C_4$–$C_{10}$ cycloalkyl or $C_6$–$C_{12}$ aromatic radical, and n is an integer greater than or equal to 1 and is such as to give a functionality ranging from 2 to 4, which comprises the re-arrangement reaction of the intermediate having general formula (II):

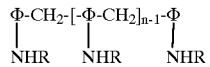
(II)

in the presence of a zeolite in acid form having a spaciousness index ranging from 2.5 to 19, extremes included.

2. The process according to claim 1, wherein the zeolites with a spaciousness index ranging from 2.5 to 19 are those consisting of synthetic crystalline material having composition (III)

(III)

wherein x is less than 1, p is an integer greater than or equal to 1, generally ranging from 1 to 20, M is a metal of groups IA, IIA, or a lanthanide, n is the valence of M, and wherein M can be partially or totally exchanged with $H^+$ or with the $(NH_4)^+$ ion or with an $(NR'_4)^+$ cation with R' an alkyl or an aryl radical.

3. The process according to claim 1 or 2, wherein the zeolites are used as such or modified by partial isomorphous substitution of aluminum with a metal selected from boron, iron or gallium or mixed with a ligand and formed into extruded pellets.

4. The process according to claim 3, wherein the zeolites are selected from beta zeolite, ZSM-12, MCM-22 and ERB-1.

5. The process according to claim 4, wherein the zeolite is beta zeolite.

6. The process according to claim 1 or 2, wherein the re-arrangement reaction takes place at a temperature ranging from 50 to 200° C.

7. The process according to claim 1 or 2, wherein the re-arrangement reaction takes place in the presence of a solvent, selected from aliphatic or aromatic hydrocarbons or from halogenated aromatic hydrocarbons and aniline.

8. The process according to claim 7, wherein the solvent is selected from aniline or chlorinated aromatic solvents.

9. The process according to claim 1 or 2, wherein the intermediate having general formula (II) contains water in a quantity less than or equal to 3% by weight.

10. A process for the preparation of diamino diphenyl methane having general formula (I)

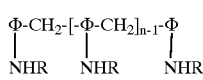
(I)

wherein Φ represents a phenyl group, R represents a hydrogen atom or a $C_1$–$C_8$ (iso)alkyl, $C_4$–$C_{10}$ cycloalkyl or $C_6$–$C_{12}$ aromatic radical, and n is an integer greater than or equal to 1 and is such as to give a functionality ranging from 2 to 4, which comprises reacting aniline, or one of its derivatives, and formaldehyde, or a compound capable of producing formaldehyde under the reaction conditions, in the presence of a zeolite in acid form having a spaciousness index ranging from 2.5 to 19.

11. The process according to claim 10, wherein the reaction is carried out with an excess of aniline, or one of its derivatives, which thus acts as reagent and solvent contemporaneously.

* * * * *